United States Patent
Whitman et al.

(10) Patent No.: US 11,813,449 B2
(45) Date of Patent: Nov. 14, 2023

(54) SEPTAL PERFORATING VEIN PACING

(71) Applicant: Medtronic, Inc., Minneapolis, MN (US)

(72) Inventors: Teresa A Whitman, Dayton, MN (US); Kenneth C. Gardeski, Inverness, FL (US); Melissa G. T. Christie, Ham Lake, MN (US); Narendra K. Simha, Falcon Heights, MN (US); Neranjan Persaud, Brooklyn Park, MN (US); Jennifer M. Bredemeier, Minneapolis, MN (US); Alexander R. Mattson, St. Paul, MN (US); Mary M. Morris, Shoreview, MN (US); Mikayle A. Holm, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 31 days.

(21) Appl. No.: 17/385,609

(22) Filed: Jul. 26, 2021

(65) Prior Publication Data
US 2022/0032042 A1 Feb. 3, 2022

Related U.S. Application Data

(60) Provisional application No. 63/059,878, filed on Jul. 31, 2020.

(51) Int. Cl.
*A61B 5/05* (2021.01)
*A61N 1/05* (2006.01)
(Continued)

(52) U.S. Cl.
CPC ............ *A61N 1/057* (2013.01); *A61B 5/0035* (2013.01); *A61B 5/055* (2013.01); *A61B 6/032* (2013.01);
(Continued)

(58) Field of Classification Search
CPC ........ A61N 1/05; A61B 5/0035; A61B 5/055; A61B 6/032; A61B 6/504; A61B 6/5247;
(Continued)

(56) References Cited

U.S. PATENT DOCUMENTS

| 4,428,378 A | 1/1984 | Anderson et al. |
| 5,052,388 A | 10/1991 | Sivula et al. |

(Continued)

FOREIGN PATENT DOCUMENTS

WO 2019/046205 3/2019

OTHER PUBLICATIONS

Kim et al., "Trans-coronary sinus intraseptal para-Hisian pacing: Cerclage pacing", Heart Rhythm, vol. 13, No. 4, Dec. 3, 2015, pp. 992-996.

(Continued)

*Primary Examiner* — Joel F Brutus
(74) *Attorney, Agent, or Firm* — Mueting Raasch Group

(57) ABSTRACT

A system and method of implanting pacing lead in a patient's heart. The system may include a catheter configured to by inserted through the coronary sinus ostium such that the distal end region of the catheter is positioned past the anterolateral vein and proximate at least one septal perforating vein. The catheter is configured to inject contrast proximate the septal perforating vein to identify an implant region for a pacing lead. Further, a controller is configured to deliver pacing therapy to the implant region.

20 Claims, 10 Drawing Sheets

(51) Int. Cl.
| | |
|---|---|
| A61M 25/00 | (2006.01) |
| A61M 5/00 | (2006.01) |
| A61B 6/03 | (2006.01) |
| A61B 6/00 | (2006.01) |
| A61B 5/00 | (2006.01) |
| A61B 5/055 | (2006.01) |
| A61N 1/375 | (2006.01) |
| A61M 25/01 | (2006.01) |
| A61M 25/10 | (2013.01) |
| A61N 1/39 | (2006.01) |
| A61M 25/09 | (2006.01) |

(52) U.S. Cl.
CPC ............ *A61B 6/504* (2013.01); *A61B 6/5247* (2013.01); *A61M 5/007* (2013.01); *A61M 25/007* (2013.01); *A61M 25/0108* (2013.01); *A61M 25/1011* (2013.01); *A61N 1/37512* (2017.08); *A61M 25/09* (2013.01); *A61N 1/0563* (2013.01); *A61N 1/3956* (2013.01); *A61N 2001/058* (2013.01)

(58) Field of Classification Search
CPC ............ A61M 25/007; A61M 25/0108; A61M 25/1011
See application file for complete search history.

(56) References Cited

U.S. PATENT DOCUMENTS

| | | | |
|---|---|---|---|
| 7,684,863 | B2 | 3/2010 | Parikh et al. |
| 8,634,919 | B1 | 1/2014 | Hou et al. |
| 10,335,589 | B2 | 7/2019 | Kim |
| 2004/0098075 | A1* | 5/2004 | Lee .................. A61N 1/056 607/122 |
| 2010/0049063 | A1 | 2/2010 | Dobak, III |
| 2019/0240019 | A1 | 8/2019 | Rafiee et al. |
| 2020/0353265 | A1 | 11/2020 | Ghosh et al. |

OTHER PUBLICATIONS

International Search Report and Written Opinion from PCT/US2021/070969 dated Nov. 3, 2021, 9 pages.
International Search Report and Written Opinion from PCT/US2021/070970 dated Nov. 11, 2021, 9 pages.
Gutleben et al., "Three-dimensional coronary sinus reconstruction-guided left ventricular lead implantation based on intraprocedural rotational angiography: a novel imaging modality in cardiac resynchronization device implantation", Europace 13, 2011, 675-682.
Kim et al., "Trans-coronary sinus intraseptal para-Hisian pacing: Cerclage pacing", Heart Rhythm Society, DOI: https://doi.org/10.1016/j.hrthm.2015.12.002, Dec. 3, 2015, 992-996.
Sommer et al., "Left and right ventricular lead positions are imprecisely determined by fluoroscopy in cardiac resynchronization therapy: a comparison with cardiac computed tomography", Europace, 16, 2014, 1334-1341.
Sun et al., "Assessment of the Coronary Venous Systems Using 256-Slice Computed Tomography", PLOS One, https://doi.org/10.1371/journal.pone.0104246, Aug. 4, 2014, 1-7.
Vijayaraman, "His-bundle Pacing to Left Bundle Branch Pacing: Evolution of His-Purkinje Conduction System Pacing", The Journal of Innovations in Cardiac Rhythm Management, 10, 2019, 3668-3673.

* cited by examiner

SEPTAL PERFORATING VEIN PACING

This application claims the benefit of U.S. Provisional Patent Application Ser. No. 63/059,878, filed on Jul. 31, 2020, which is incorporated by reference herein in its entirety.

The disclosure herein relates to systems, devices, and methods of pacing of cardiac tissue, and more particularly, to pacing the cardiac conduction system of the heart within or proximate a septal perforating vein.

Implantable medical devices (IMDs), such as cardiac pacemakers or implantable cardioverter defibrillators, deliver therapeutic stimulation to patients' hearts thereby improving the lives of millions of patients living with heart conditions. Conventional pacing techniques involve pacing one or more of the four chambers of patient's heart—left atrium (LA), right atrium (RA), left ventricle (LV), and right ventricle (RV). One common conventional therapeutic pacing technique that treats a slow heart rate, referred to as Bradycardia, involves delivering an electrical pulse to a patient's right ventricular tissue. In response to the electrical pulse, both the right and left ventricles contract. However, the heart beat process may be significantly delayed because the pulse travels from the right ventricle through the left ventricle. The electrical pulse passes through the muscle cells that are referred to as myocytes. Myocyte-to-myocyte conduction may be very slow. Delayed electrical pulses can cause the left ventricle to be unable to maintain synchrony with the right ventricle.

Over time, the left ventricle can become significantly inefficient at pumping blood to the body. In some patients, heart failure can develop such that the heart is too weak to pump blood to the body. Heart failure may be a devastating diagnosis since, for example, fifty percent of the heart failure patients have a life expectancy of five years. To avoid the potential development of heart failure, some physicians have considered alternative pacing methods that involve the cardiac conduction system. The cardiac conduction system, like a "super highway," may be described as quickly conducting electrical pulses whereas pacing cardiac muscle tissue may slowly conduct electrical pulses, like "traveling on a dirt road."

The cardiac conduction system includes sinoatrial node (SA node), atrial internodal tracts (i.e., anterior internodal, middle internodal, and posterior internodal), atrioventricular node (AV node), His bundle (also known as atrioventricular bundle or bundle of His), and right and left bundle branches. The SA node, located at the junction of the superior vena cava and right atrium, is considered to be the natural pacemaker of the heart since it continuously and repeatedly emits electrical impulses. The electrical impulse spreads through the muscles of right atrium to left atrium to cause synchronous contraction of the atria. Electrical impulses are also carried through atrial internodal tracts to atrioventricular (AV) node—the sole connection between the atria and the ventricles. Conduction through the AV nodal tissue takes longer than through the atrial tissue, resulting in a delay between atrial contraction and the start of ventricular contraction. The AV delay, which is the delay between atrial contraction and ventricular contractor, allows the atria to empty blood into the ventricles. Then, the valves between the atria and ventricles close before causing ventricular contraction via branches of the bundle of His (or His bundle). The His bundle is located in the membranous atrioventricular septum near the annulus of the tricuspid valve. The His bundle splits into right and left bundle branches and are formed of specialized fibers called "Purkinje fibers." Purkinje fibers may be described as being able to rapidly conduct an action potential down to the ventricular septum (VS), spread the depolarization wavefront quickly through the remaining ventricular myocardium, and produce a coordinated contraction of the ventricular muscle mass.

While His bundle pacing is increasingly used as an alternative to traditional pacing techniques, His bundle pacing has not been widely adopted for a variety of reasons. For example, His pacing electrodes should be positioned within a precise target location (e.g., within about 1 millimeter) of the His bundle, which may be difficult. Further, some physicians place a lead in a proximal His bundle position that requires a much higher pacing output to be delivered by the pacemaker to effectively pace the His bundle. Placing the pacing lead near the conduction system neighboring the His bundle may also have beneficial effects. It is desirable to develop new methods and systems of identifying an appropriate implant region to position a pacing lead therein.

SUMMARY

Typical pacing options, including, e.g., cardiac resynchronization therapy (CRT), are often limited in part by the venous locations that a pacing lead can be delivered to. For example, often, a CRT pacing lead may be delivered to the lateral or posterior lateral veins. The illustrative systems, devices, and methods described herein may be configured to assist a user (e.g., a physician) in delivering a CRT-type pacing lead deeper into the coronary venous system than current therapies to pace the native conduction system (e.g., the bundle branches). For example, the pacing lead may be positioned in a tributary of the anterior interventricular vein, such as a septal perforating vein, to pace the right and left bundle branches. As such, the pacing lead may not extend across a valve, may not be dependent on direction of approach to the septal wall, and may not damage either of the bundle branches.

Specifically, the illustrative systems, devices, and methods described herein may include illuminating the pathway to access the native conduction system through the venous system. For example, a "roadmap" for the great cardiac vein may be created to help identify at least one septal perforating vein through which a pacing lead may be delivered to the bundle branches of the heart. The "roadmap" may be created using localized or selective vein contrast injections (e.g., via balloon catheter) into the coronary venous system to help illuminate the deep structure of the branch veins (e.g., anterior interventricular and septal perforating veins). Localized or selective vein contrast injections allow for a reduction in volume of contrast agent injected into the body, which results in a more efficient use of contrast agent and reduces any undesirable effect associated with large volumes of contrast agent within the body.

One illustrative method of implanting pacing lead in a patient's heart may include inserting a catheter through coronary sinus ostium of the patient's heart. The method may also include moving the catheter to position a distal end region of the catheter into the great cardiac vein past the anterolateral vein of the patient to one or more positions proximate at least one septal perforating vein of the patient. The method may also include injecting contrast out of the distal end region of the catheter into an injection area of each of the one or more positions proximate the at least one septal perforating vein. Further, the method may include identifying an implant region proximate the at least one septal perforating vein, removing the catheter, and moving a pacing lead to the implant region to deliver pacing therapy thereto.

One illustrative method of identifying an implant region in a patient's heart may include inserting a catheter through the coronary sinus ostium of the patient's heart. The method may also include moving the catheter to position a distal end region of the catheter into the great cardiac vein past the anterolateral vein of the patient to one or more positions proximate at least one septal perforating vein of the patient. The catheter may include a distal balloon and a proximal balloon positioned on the distal end region. The distal balloon may be located more distally than the proximal balloon. Further, the method may include inflating the distal and proximal balloons to block blood flow to an injection area between the distal and proximal balloons at each of the one more positions. The method may include injecting contrast out of the distal end region of the catheter into an injection area of each of the one or more positions proximate the at least one septal perforating vein. The method may also include identifying an implant region proximate the at least one septal perforating vein.

One illustrative catheter may include an elongate housing and at least two inflatable balloons. The elongate housing may extend between a proximal end region and a distal end region and positionable in the great cardiac vein such that the distal end region is located past the anterolateral vein of the patient proximate at least one septal perforating vein of the patient. The elongate housing may define a lumen extending therethrough. The elongate housing may further define one or more side openings extending through an outer surface of the elongate housing in the distal end region of the elongate housing and in fluid communication with the lumen. Contrast may be configured to be injected through the one or more side openings of the elongate housing into an injection area proximate the at least one septal perforating vein. The at least two inflatable balloons may be positioned on the distal end region of the elongate housing. The at least two inflatable balloons may include a first inflatable balloon positioned distally of the one or more side openings and a second inflatable balloon positioned proximally of the one or more side openings.

One illustrative pacing device may include a pacing lead and a controller. The pacing lead may extend between a proximal end region and a distal end region. The pacing lead may include a plurality of electrodes proximate the distal end region. The distal end region of the pacing lead may be positionable in an implant region proximate at least one septal perforating vein of a patient's heart. The controller may include one or more processors and operably coupled to the pacing lead. The controller may be configured to deliver pacing therapy to the implant region proximate the at least one septal perforating vein of the patient's heart using at least one electrode of the plurality of electrodes of the pacing lead.

One illustrative system for delivering pacing therapy to a patient's heart may include a catheter, a pacing lead, and a controller. The catheter may include an elongate housing extending between a proximal end region and a distal end region. The elongate housing may define a lumen extending therethrough. The catheter may be configured to be inserted through the coronary sinus ostium of a patient's heart such that the distal end region of the catheter is positioned into the great cardiac vein past the anterolateral vein of the patient proximate at least one septal perforating vein of the patient's heart. The catheter may be further configured to inject contrast into an injection area proximate the at least one septal perforating vein. The pacing lead may extend between a proximal end region and a distal end region. The pacing lead may include a plurality of electrodes proximate the distal end region. The distal end region of the pacing lead may be positionable in an implant region proximate the at least one septal perforating vein and the injection area. The controller may be operably coupled to the pacing lead and may be configured to deliver pacing therapy to the implant region, through at least one electrode of the plurality of electrodes, when the distal end region of the pacing lead is positioned in the implant region.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF ILLUSTRATIVE EMBODIMENTS

Figure 1:
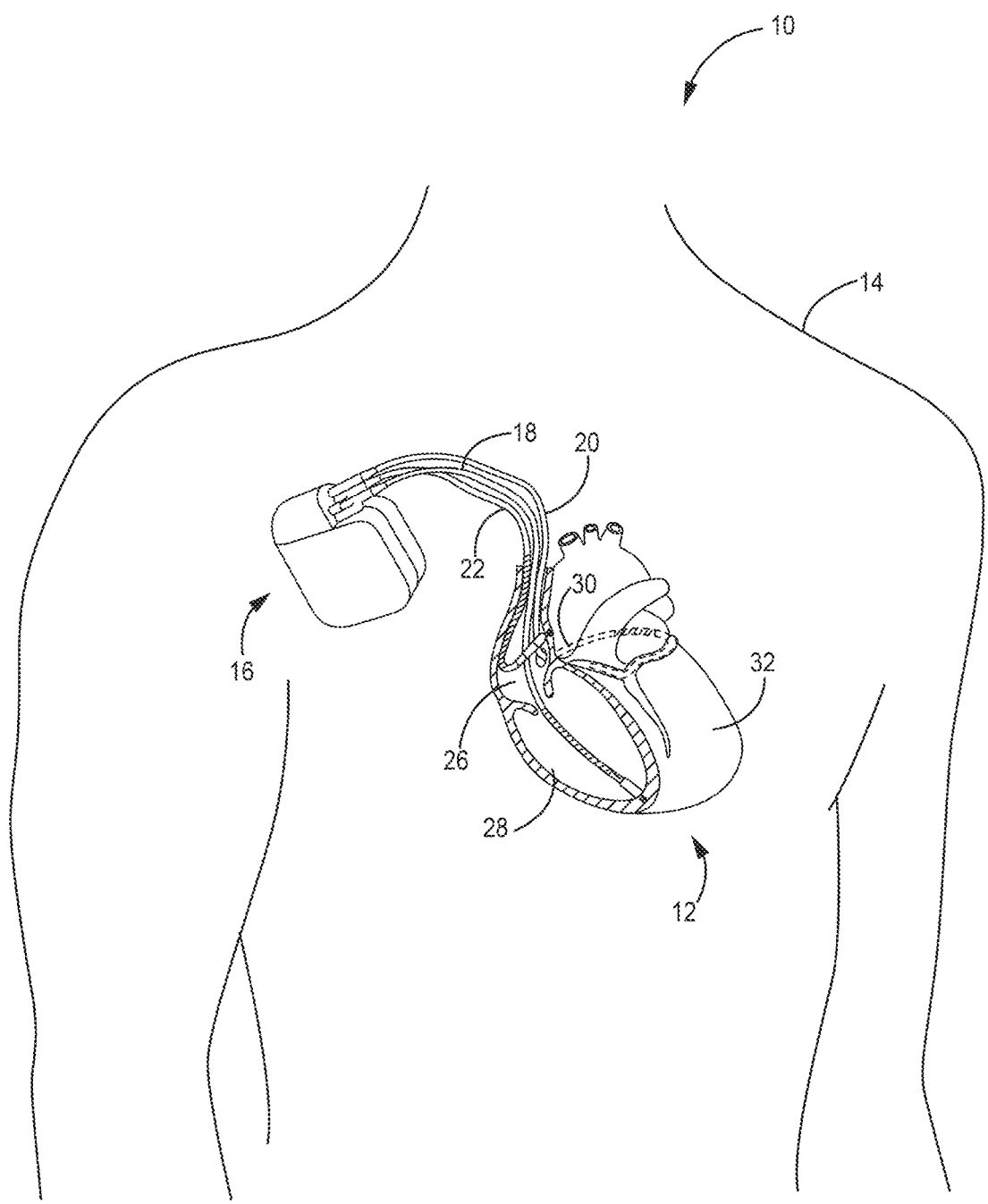
FIG. 1 is a diagram of an illustrative system including an illustrative implantable medical device (IMD).

In the following detailed description of illustrative embodiments, reference is made to the accompanying figures of the drawing which form a part hereof, and in which are shown, by way of illustration, specific embodiments which may be practiced. It is to be understood that other embodiments may be utilized and that structural changes may be made without departing from (e.g., still falling within) the scope of the disclosure presented hereby.

Illustrative cardiac therapy systems, devices, and methods may be described herein with reference to FIGS. 1-9. It will be apparent to one skilled in the art that elements or processes from one embodiment may be used in combination with elements or processes of the other embodiments, and that the possible embodiments of such systems, devices, and methods using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

An illustrative therapy system 10 that may be used to deliver pacing therapy to a patient 14 is illustrated in a conceptual diagram of FIG. 1. Patient 14 may, but not necessarily, be a human. The therapy system 10 may include an implantable medical device 16 (IMD), which may be coupled to leads 18, 20, 22. The IMD 16 may be, e.g., an implantable pacemaker, cardioverter, and/or defibrillator, that delivers, or provides, electrical signals (e.g., paces, etc.) to and/or senses electrical signals from the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the septum between the left and right ventricles 32, 28 of the heart 12. More specifically, the LV coronary sinus lead 20 may extend through the coronary sinus ostium and past the anterolateral vein to one or more positions proximate at least one septal perforating vein of the patient, as described further herein. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., A-V delay and other various timings, pulse width, amplitude, voltage, burst length, etc. Further, the IMD 16 may be operable to use various electrode configurations to deliver pacing therapy, which may be unipolar, bipolar, quadripoloar, or further multipolar. For example, a multipolar lead may include several electrodes that can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

Figure 2:
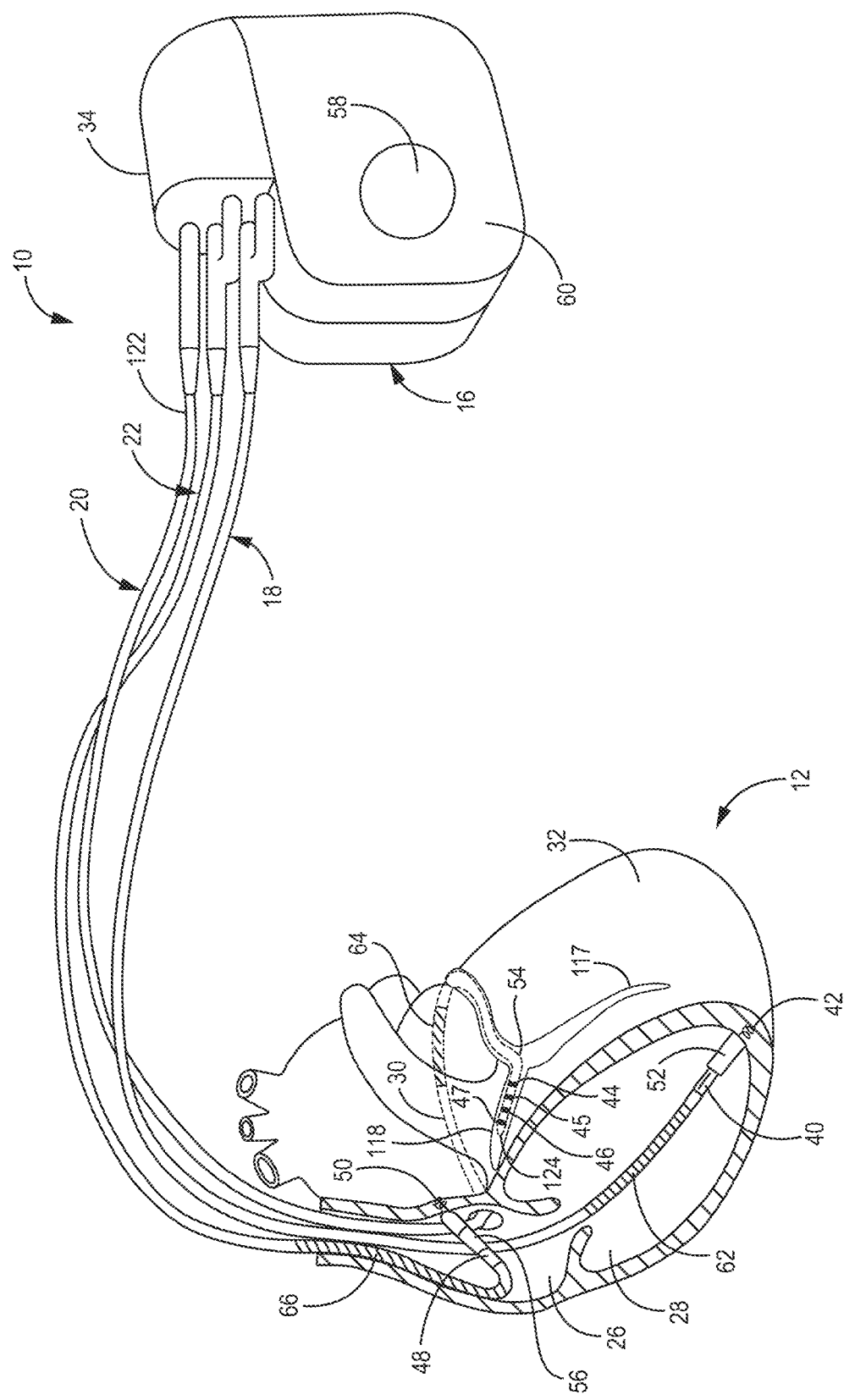
FIG. 2 is a diagram of the illustrative IMD of FIG. 1.

FIG. 2 is a conceptual diagram illustrating the IMD 16 and the leads 18, 20, 22 of therapy system 10 of FIG. 1 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, bipolar electrodes 44, 45, 46, 47 are located proximate to a distal end of the lead 20 and bipolar electrodes 48, 50 are located proximate to a distal end of the lead 22.

The electrodes 40, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to a respective one of the electrical contacts on the proximal end of the leads 18, 20, 22.

Additionally, electrodes 44, 45, 46 and 47 may have an electrode surface area of about 5.3 $mm^2$ to about 5.8 $mm^2$. Electrodes 44, 45, 46, and 47 may also be referred to as LV1, LV2, LV3, and LV4, respectively. The LV electrodes (i.e., left ventricle electrode 1 (LV1) 44, left ventricle electrode 2 (LV2) 45, left ventricle electrode 3 (LV3) 46, and left ventricle 4 (LV4) 47 etc.) on the lead 20 can be spaced apart at variable distances. For example, electrode 44 may be a distance of, e.g., about 21 millimeters (mm), away from electrode 45, electrodes 45 and 46 may be spaced a distance of, e.g. about 1.3 mm to about 1.5 mm, away from each other, and electrodes 46 and 47 may be spaced a distance of, e.g. 20 mm to about 21 mm, away from each other.

The electrodes 40, 42, 44, 45, 46, 47, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. Further, in some examples, the IMD 16 may also deliver pacing pulses via the electrodes 40, 42, 44, 45, 46, 47, 48, 50 configured to pace the cardiac conduction system of the patient's heart 12. In some examples, as illustrated in FIG. 2, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48, 50 may be used for unipolar sensing or pacing in combination with the housing electrode 58. It is generally understood by those skilled in the art that other electrodes can also be selected to define, or be used for, pacing and sensing vectors. Further, any of electrodes 40, 42, 44, 45, 46, 47, 48, 50, 58, when not being used to deliver pacing therapy, may be used to sense electrical activity during pacing therapy.

As described in further detail with reference to FIG. 2, the housing 60 may enclose a therapy delivery module that may include a stimulation generator for generating cardiac pacing pulses and defibrillation or cardioversion shocks, as well as a sensing module for monitoring the electrical signals of the patient's heart (e.g., the patient's heart rhythm). The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58, or defibrillation electrode-to-housing electrode vector).

The configuration of the illustrative therapy system 10 illustrated in FIGS. 1 and 2 is merely one example. In other examples, the therapy system may include epicardial leads and/or patch electrodes instead of or in addition to the transvenous leads 18, 20, 22 illustrated in FIG. 1. Additionally, in other examples, the therapy system 10 may be implanted in/around the cardiac space without transvenous leads (e.g., leadless/wireless pacing systems) or with leads implanted (e.g., implanted transvenously or using approaches) into the left chambers of the heart (in addition to or replacing the transvenous leads placed into the right chambers of the heart as illustrated in FIG. 1). Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 1 and 2. Still further, other therapy systems may include a single lead that extends from the IMD 16 into the right atrium 26 or the right ventricle 28, or two leads that extend into a respective one of the right atrium 26 and the right ventricle 28.

Figure 3:
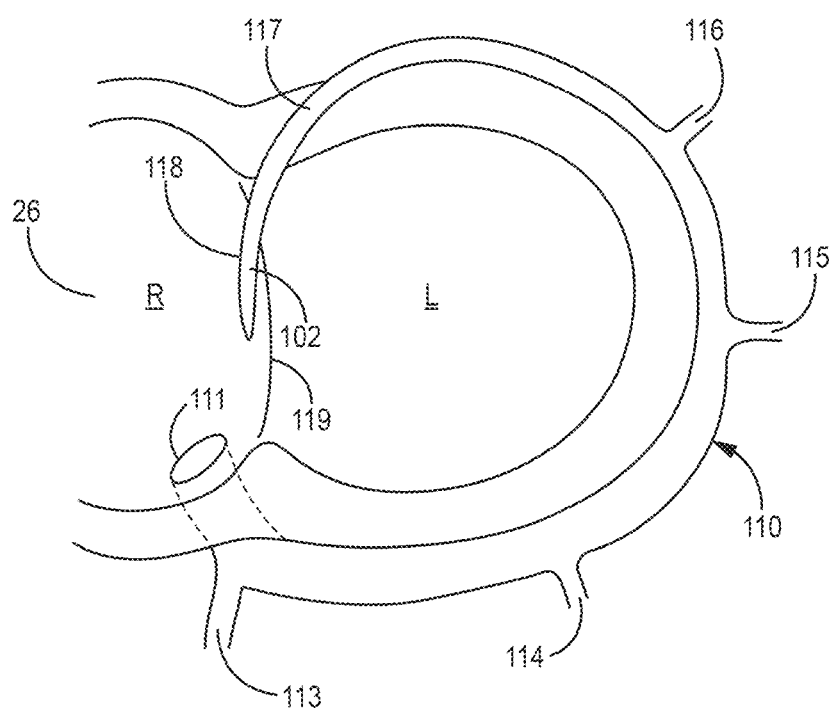
FIG. 3 illustrates a coronary vein anatomy.

Specifically, in one or more embodiments, the therapy system may include a single lead (e.g., transvenous lead 20) that extends through the coronary sinus ostium and past the anterolateral vein to one or more positions proximate at least one septal perforating vein of the patient, as described further herein. For example, as shown in FIG. 2, the transvenous lead 20 may extend into the septal perforating vein 118 that branches from the anterior interventricular vein 117. Further, FIG. 3 illustrates the coronary vein anatomy with various regions of the great cardiac vein 110 depicted to illustrate the location of at least one septal perforating vein 118 into which the pacing lead is positioned. The great cardiac vein 110 extends from the coronary sinus ostium 111 defined by the wall of the right atrium 26 and past the middle cardiac vein 113, the posterolateral vein 114, the lateral vein 115, the anterolateral vein 116, and the anterior interventricular vein 117. The anterior interventricular vein 117 then branches off into at least one septal perforating vein 118 proximate the ventricular septum 119. The at least one septal perforating vein 118 may provide access to an implant region 102 proximate the bundle branches of the heart such that a pacing lead may deliver pacing therapy thereto.

During CRT procedures, the coronary venous system may be injected with a contrast agent such that the characteristics and/or regions of the great cardiac vein 110 may be identified via imaging. However, the systems, devices, and methods described herein include delivering a pacing lead deeper into the coronary venous system, therefore, typically-used contrast injections may be insufficient. For example, typically-used contrast injections may not be able to inject contrast agent into the septal perforating vein or may need to deliver a higher-pressure, larger dose of contrast agent to ensure that the contrast agent enters the septal perforating vein. Both scenarios may be undesirable because either the septal perforating vein is not illuminated for positioning the pacing lead or the increased dose of contrast agent may be less optimal for the patient.

Figure 6:
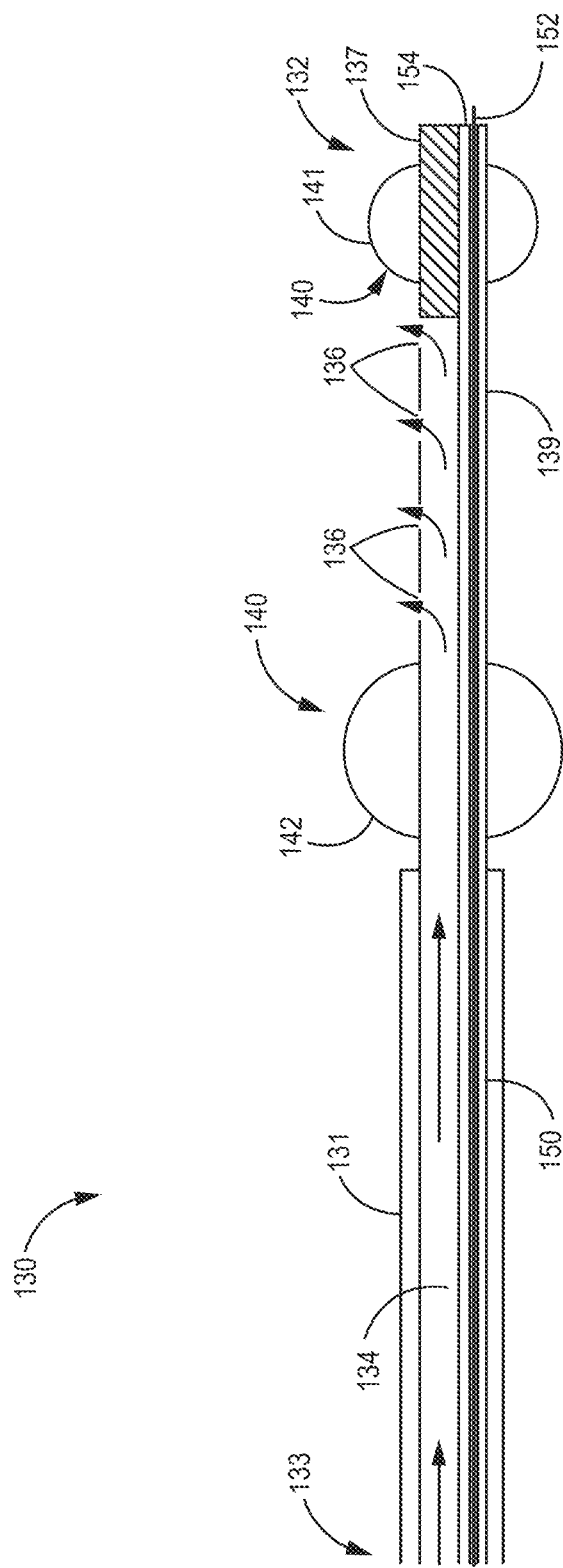
FIG. 6 is a cross-sectional diagram of an illustrative catheter.

Therefore, as will be further described herein, a catheter 130 (e.g., as shown in FIG. 6) may be used to navigate the great cardiac vein 110 and inject a contrast agent to help locate an implant region within the at least one septal perforating vein 118. The catheter may be positioned at one or more positions within the great cardiac vein 110 to inject relatively small doses of contrast (e.g., less than or equal to 10 milliliters) to identify the implant region. In other words, the contrast agent may be injected at a first position within the great cardiac vein 110 and if the implant region (e.g., within the septal perforating vein 118) is properly illuminated/identified, the procedure may continue (e.g., by inserting a pacing lead to the implant region). However, if the implant region is not properly illuminated/identified, the catheter may be moved to another location to inject the contrast agent. The catheter may be moved to one or more positions, injecting the contrast agent at each position, to illuminate and identify the implant region.

Figure 7:
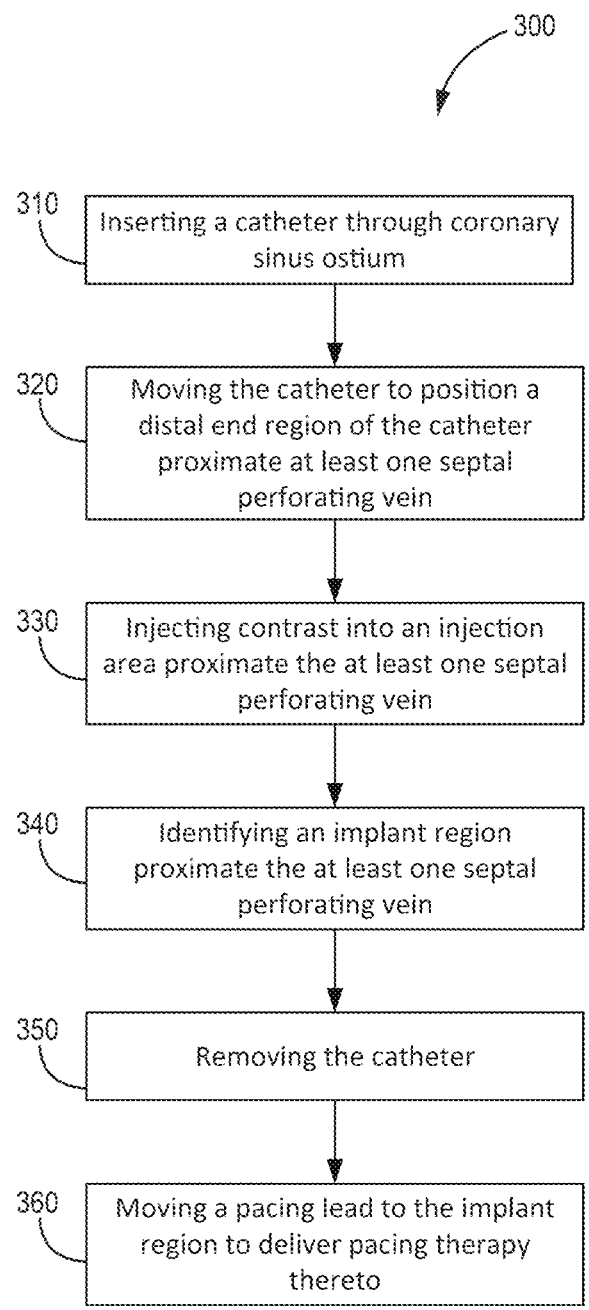
FIG. 7 is a flow diagram of an illustrative method of implanting a pacing lead in a patient's heart.

Specifically, as shown in the block diagram of FIG. 7, the method 300 of implanting a pacing lead in a patient's heart may include inserting 310 a catheter (e.g., catheter 130 illustrated in FIG. 6) through the coronary sinus ostium of the patient's heart. Further, the method 300 may include moving 320 the catheter to position a distal end region of the catheter into the great cardiac vein past the anterolateral vein of the patient to one or more positions proximate at least one septal perforating vein of the patient. The method 300 may also include injecting 330 contrast out of the distal end region of the catheter into an injection area of each of the one or more positions proximate the at least one septal perforating vein and identifying 340 an implant region proximate the at least one septal perforating vein. Therefore, the catheter may be moved to one or more positions to inject contrast in an effort to identify the implant region. In one or more embodiments, the catheter may be moved to a plurality of distinct positions within the great cardiac vein.

By injecting contrast at one or more positions proximate the at least one septal perforating vein, the user may be able to create a great cardiac vein map to help visualize the at least one septal perforating vein. For example, multiple mini-venograms may be produced from imaging of the heart while injecting contrast agent at the one or more positions. In one or more embodiments, the mini-venograms may be combined or stitched together to form a larger picture of the coronary venous system. For example, software may be used to form a single, complete venogram that may, in one or more embodiments, serve as a "roadmap" throughout the procedure.

Furthermore, the method 300 may include removing 350 the catheter and moving 360 a pacing lead to the implant region to deliver pacing therapy thereto. For example, after identifying the implant region proximate the at least one septal perforating vein (e.g., proximate the bundle branches, His bundle, etc.), the pacing lead may be inserted through the great cardiac vein to the implant region (e.g., using visual images generated from the injection of the contrast agent therein). Once the pacing lead is properly positioned, the pacing lead may deliver pacing therapy to the heart. For example, in one or more embodiments, the implant region may provide cardiac conduction system pacing such that the pacing lead may deliver pacing to the cardiac conduction system pacing of the heart at the implant region. In one or more embodiments, the implant region may be proximate the His bundle such that the pacing lead may deliver His bundle pacing to the implant region. In one or more embodiments, the implant region may be proximate the left bundle branch pacing such that the pacing lead delivers left bundle branch pacing to the implant region. In other embodiments, the implant region may provide traditional cardiac pacing. For example, in an ovine study, cardiac conduction system pacing from the septal perforating vein may be achieved with about a 2.0V threshold, impedance of about 362 ohms, and a current of about 7.0 mA. Further, in one or more embodiments, cardiac conduction system pacing from the septal perforating vein may be achieved with about a 1.8V threshold, an R-wave of about 1.4 mV, and a pulse width of about 0.4 ms.

In one or more embodiments, once the pacing lead is positioned, the method may further include generating a cardiac map of electrical activation based on a plurality of electrode signals monitored using a plurality of external electrodes proximate the skin on the patient such as, e.g., described in U.S. Provisional Patent Application Ser. No. 62/844,489 filed on May 7, 2019, entitled "Supplementation of Cardiac Conduction System Pacing Therapy." In other words, the operability of the pacing lead may be verified after the pacing lead is positioned within the heart using various systems such as those that provide cardiac maps of electrical activation. Further in one or more embodiments, electrical activation mapping may be provided using, e.g., ECG, Vectorcardiography, 3D electrical mapping, etc. Specifically, electrical activation mapping may be provided by software including, e.g., CardioInsight, Ensite, and CARTO.

One illustrative catheter 130 for the methods described herein is illustrated in FIG. 6. The catheter 130 may include an elongate housing 131 extending between a proximal end region 133 (e.g., including a proximal end) and a distal end region 132 (e.g., including a distal end 137). It is noted that the proximal end of the catheter 130 may be out of frame in FIG. 6, but the most proximal portion of the catheter is denoted with reference numeral 133 (e.g., even though the proximal end region 133 may also be out of frame). The elongate housing 131 of the catheter 130 may be positionable in the great cardiac vein such that the distal end region 132 may be located past the anterolateral vein of the patient proximate at least one septal perforating vein of the patient. To be positionable in the great cardiac vein such that the distal end region 132 may be located past the anterolateral vein of the patient proximate at least one septal perforating vein of the patient, the catheter 130 may comprise various specific materials and define a relatively small size. For example, the elongate housing 131 may include (e.g., be formed of) any suitable materials such as, e.g., polyurethane, silicone, a hybrid of polyurethane and silicone, etc. Also, for example, the elongate housing 131 may define any suitable cross-sectional diameter. Thus, the elongate housing 131 may define a cross-sectional diameter such that the catheter 130 may be inserted into the great cardiac vein proximate the at least one septal perforating vein. Such cross-sectional diameter of the elongate housing 131 may be smaller than many other traditionally-used catheters because, for example, the amount of space in the great cardiac vein proximate the at least one septal perforating vein may be substantially smaller than where traditional catheters and/or leads have been navigated and/or placed within the venous system.

The elongate housing 131 may define a lumen 134 extending therethrough (e.g., between the distal and proximal end regions 132, 133). Further, the elongate housing 131 may define one or more side openings 136 extending through an outer surface 139 of the elongate housing 131 in the distal end region 132 of the elongate housing 131 and in fluid communication with the lumen 134. The catheter 130 may be configured such that contrast may be injected through the one or more side openings 136 (e.g., from the lumen 134) of the elongate housing 131 into an injection area proximate the at least one septal perforating vein. Although the openings through which contrast is injected is described as "side" openings, in one or more embodiments, the openings through which contrast is injected may be located at the distal end of the elongate housing 131.

Further, in one or more embodiments, the catheter 130 may include at least two inflatable balloons 140 positioned on (e.g., near, proximate, etc.) the distal end region 132 of the elongate housing 131. The at least two inflatable balloons 140 may include a first inflatable balloon 141 positioned distally of the one or more side openings 136 and a second inflatable balloon 142 positioned proximally of the one or more side openings 136. In other words, the first inflatable balloon 141 may be located closer to the distal end 137 than the second inflatable balloon 142. As shown in FIG. 6, the one or more side openings 136 may include multiple openings between the first and second balloons 141, 142. The at least two inflatable balloons 140 may be configured to inflate to block blood flow in the great cardiac vein to the injection area between the first and second balloons 141, 142 prior to injecting contrast into the injection area. In one or more embodiments, the elongate housing 131 may further define a bypass lumen that is configured to allow blood to pass through the catheter 130 without interfering with the contrast injection through the one or more side openings 136.

The at least two inflatable balloons 140 may include (e.g., be formed of) any suitable material such as, e.g., a compliant material. The at least two inflatable balloons 140 may define any suitable diameter when inflated. In one or more embodiments, the first balloon 141 may define a first diameter when inflated and the second balloon 142 may define a second diameter when inflated, the first diameter being the same as or different from the second diameter. For example, the first diameter and/or second diameter may be any suitable diameter. In one or more embodiments, the first diameter may be smaller than the second diameter (e.g., because the first balloon 141 may be deeper inside the vein due to its distal location on the elongate housing 131).

The first and second inflatable balloons 141, 142 may be separated by any suitable distance along the elongate housing 131. For example, the first and second inflatable balloons 141, 142 may be spaced apart by about 0.5 inches to 1 inch (e.g., measured between the closest portions of the first and second inflatable balloons 141, 142). The distance between the at least two inflatable balloons 140 may determine the precision of the catheter 130 when injecting contrast to identify the at least one septal perforating vein. For example, if the balloons are closer together, the contrast may be injected with a more targeted approach and, e.g., use less contrast agent. If the balloons are farther apart, the contrast may be injected with a wider scope but may use more contrast agent.

In some embodiments, the catheter 130 may include more than two inflatable balloons. For example, the at least two inflatable balloons 140 may include a third balloon and a fourth balloon. Specifically, the third balloon may be positioned along the elongate housing 131 more proximal than the second balloon 142, and the fourth balloon more proximal than the third balloon. The third and fourth balloons may have similar characteristics as described in connection with the first and second balloons 141, 142 (e.g., size, material, spacing). Further, the one or more side openings 136 may include a first opening located between the first and second balloons 141, 142 and a second opening located between the third and fourth balloons. The contrast agent may be injected through both of the first and second openings to assist in identifying the implant region. The at least two inflatable balloons 140 may include any suitable number of balloons in any suitable arrangement (e.g., three inflatable balloons with an opening between the first and second balloons and another opening between the second and third balloons).

In one or more embodiments, the catheter 130 may include one or more markers disposed on the elongate housing 131 such that portions of the catheter 130 may be identified using imaging during a procedure. For example, the catheter 130 may include any type of marker such as, e.g., a radiopaque marker, a directional marker, a mapping electrode, any suitable fluoro-visible marker, etc. The one or more markers may be positioned at any suitable location along the elongate housing 131. For example, the catheter 130 may include at least one marker associated with each inflatable balloon (e.g., on either side of each balloon) such that the balloons are easily identifiable using imaging. Also, for example, the one or more markers may be located along the elongate housing 131 to help identify an opening through which contrast or a guide wire may extend.

Further, in one or more embodiments, the elongate housing 131 of the catheter 130 may define a guide wire lumen 150 and the catheter 130 may include a guide wire 152 configured to extend through the guide wire lumen 150. The guide wire 152 may be used to help position the pacing lead within the at least one septal perforating vein after the implant region is identified. For example, a guide wire 152 may be inserted through the catheter 130 (e.g., through the guide wire lumen 150) into position proximate the identified implant region before the catheter 130 is removed from the great cardiac vein (e.g., while the guide wire 152 is retained proximate the septal perforating vein). Next, the pacing lead may be moved to the implant region using the guide wire 152 (e.g., the pacing lead may be guided along the guide wire 152).

The elongate housing 131 may define a guide wire opening 154 extending through the outer surface 139 of the elongate housing 131 and in fluid communication with the guide wire lumen 150 such that the guide wire 152 exits the guide wire lumen 150 through the guide wire opening 154. Because the guide wire 152 may be used to assist in guiding the pacing lead into the at least one septal perforating vein, it may be desirable to align the guide wire 152 with the at least one septal perforating vein. In one or more embodiments, the guide wire opening 154 may be positioned between the first and second balloons 141, 142. Further, the guidewire opening 154 may be positioned such that the opening is aligned with the at least one septal perforating vein (e.g., using the one or more markers). Therefore, the guide wire 152 may exit the guide wire opening 154 directly into the at least one septal perforating vein. In one or more embodiments, the guide wire opening 154 may be positioned at the distal end of the elongate housing 131 (e.g., as shown in FIG. 6) such that the guide wire 152 may exit the distal end of the elongate housing 131. In such embodiments, the guide wire 152 may be pulled proximally by a set distance (e.g., to clear the branch vein of interest) such that the guide wire 152 may be aligned with the at least one septal perforating vein (e.g., so that the pacing lead may be directed therein).

Further, in one or more embodiments, the catheter 130 may be used to navigate the coronary venous system (e.g., into the at least one septal perforating vein). For example, the distal end region 132 of the catheter 130 may define a spiral tip to, e.g., navigate the at least one septal perforating vein. The spiral tip may utilize a rotate-to-advance principle similar to an Archimedes' screw, but where the auger advances as it is rotated. Also, in one or more embodiments, an actively steerable catheter may be used to navigate the at least one septal perforating vein. For example, after positioning the guide wire 152 and removing the catheter 130, the actively steerable catheter may be inserted through the great cardiac vein using the guide wire 152 to the at least one septal perforating vein. Thereafter, the actively steerable catheter may be used to navigate the at least one septal perforating vein to the implant region (e.g., using imaging of the vein, which may be illuminated due to the contrast agent injected therein). The actively steerable catheter may include any catheter designed such that the distal tip deflects at the direction of the user to navigate a vessel (e.g., tortuous path of a vein).

Figure 8:
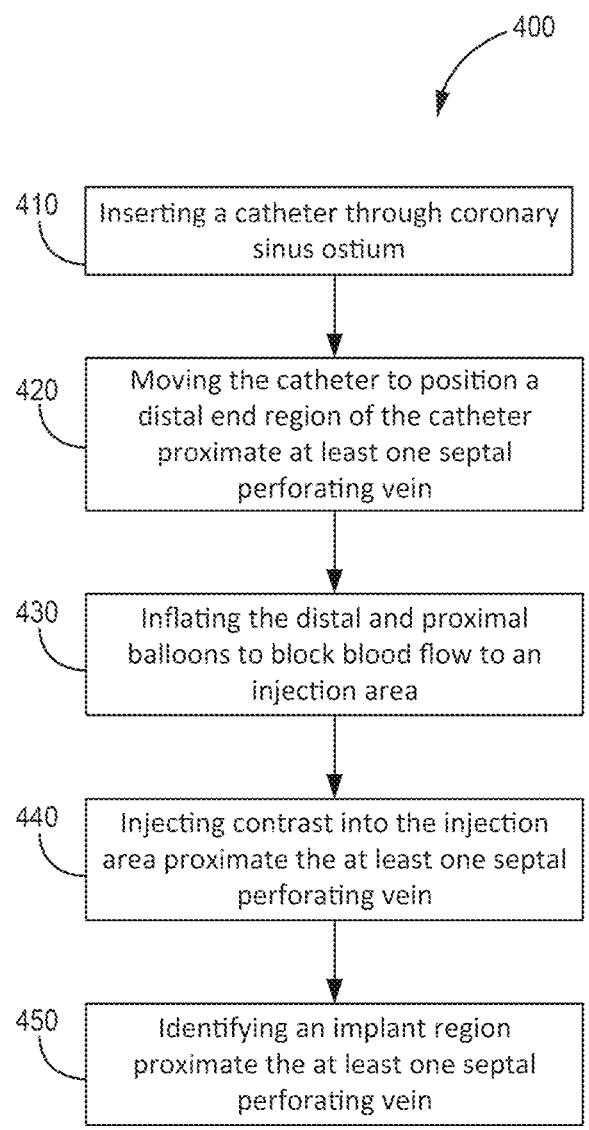
FIG. 8 is a flow diagram of an illustrative method of identifying an implant region in a patient's heart.

These components of the catheter 130 are further described in a method 400 of identifying an implant region in a patient's heart (e.g., using the catheter 130) as illustrated in the block diagram of FIG. 8. The method 400 may include inserting 410 the catheter through the coronary sinus ostium of the patient's heart. Further, the method 400 may include moving 420 the catheter to position a distal end region of the catheter into the great cardiac vein past the anterolateral vein of the patient to one or more positions proximate at least one septal perforating vein of the patient. The catheter may include a distal balloon (e.g., the first balloon 141) and a proximal balloon (e.g., the second balloon 142) positioned on the distal end region, as described herein in connection with FIG. 6. The distal balloon may be located more distally than the proximal balloon. The method 400 may also include inflating 430 the distal and proximal balloons to block blood flow to an injection area between the distal and proximal balloons at each of the one or more positions. Also, the method 400 may include injecting 440 contrast out of the distal end region (e.g., through the one or more side openings 136) of the catheter into the injection area of each of the one or more positions proximate the at least one septal perforating vein and identifying 450 an implant region proximate the at least one septal perforating vein (e.g., such that the pacing lead can be positioned at the identified implant region as described herein).

The illustrative methods may include moving the catheter to one or more positions because it may take one or more placements and injections of contrast to identify the implant region proximate the at least one septal perforating vein. In other words, the catheter may be moved and the contrast agent injected into the vein multiple times before the implant region is identified. For example, in one or more embodiments, after inflating the balloons and injecting contrast, the distal and proximal balloons may be deflated and the catheter may be moved to another position of the one or more positions. Thereafter, the distal and proximal balloons may be inflated again to block blood flow to another injection area between the balloons and contrast may be injected into the injection area of the another position of the one or more positions proximate the at least one septal perforating vein.

Figure 4:
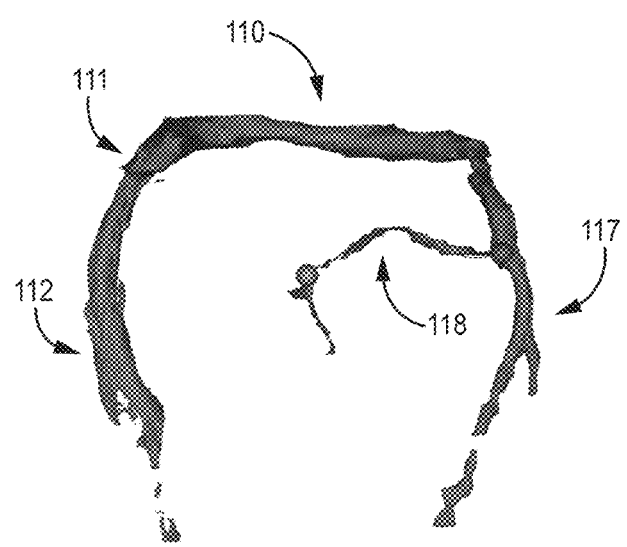
FIG. 4 illustrates a segmented cardiac computed tomography (CT) image showing a portion of the coronary venous system from the right anterior oblique (RAO) 60 fluoroscopic view.

In one or more embodiments, prior to inserting the catheter through the coronary sinus ostium of the patient's heart, the user may generate images of the coronary venous system as a preliminary view for helping navigate with the catheter to, e.g., help determine where to further inject contrast to identify the implant region proximate the at least one septal perforating vein. Generating an image of the patient's heart may be done in any suitable way. For example, the image of the patient's heart may be generated using a CT/MR angiography scope, rotational angiography, ultrasound, x-ray, etc. For example, FIG. 4 illustrates a segmented cardiac computed tomography (CT) image showing a portion of the coronary venous system from the right anterior oblique (RAO) 60 fluoroscopic view. These preliminary views may be helpful in determining the position of the imaging crosshead according to the preferred view prior to inserting the catheter.

Figure 5:
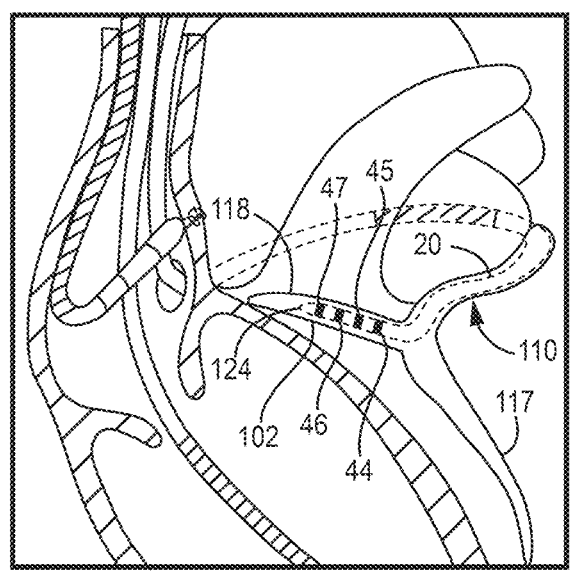
FIG. 5 is a diagram of an enlarged view of a region of FIG. 2 illustrating a distal end of the electrical lead disposed in at least one septal perforating vein.

After the implant region is identified and the catheter is removed, the user may move a pacing lead to the implant region to deliver pacing therapy thereto. One illustrative pacing lead 20 located within the at least one septal perforating vein 118 and for delivery pacing therapy as described herein is illustrated in FIG. 5 (e.g., an expanded view of FIG. 2). The pacing lead 20 may extend between a proximal end region 122 (e.g., proximate the IMD 16 illustrated in FIG. 2) and a distal end region 124. The pacing lead 20 may include a plurality of electrodes (e.g., electrodes 44, 45, 46, 47) proximate the distal end region 124. The distal end region 124 of the pacing lead 20 may be positionable in an implant region proximate at least one septal perforating vein 118 of a patient's heart. Specifically, the electrodes may be spaced for efficiently capturing both the right and left bundle branches from the septal perforating vein 118.

The distal end region 124 of the pacing lead 20 may define any suitable cross-sectional diameter. For example, the cross-sectional diameter of the distal end region 124 of the pacing lead 20 may sized to be inserted into the at least one septal perforating vein 118 such that the electrodes may be proximate the implant region. Specifically, the distal end region 124 of the pacing lead 20 may define a cross-sectional diameter of about less than or equal to 1 millimeter. More specifically, the pacing lead may be described as a 1-3 French (Fr) lead.

Figure 9A:
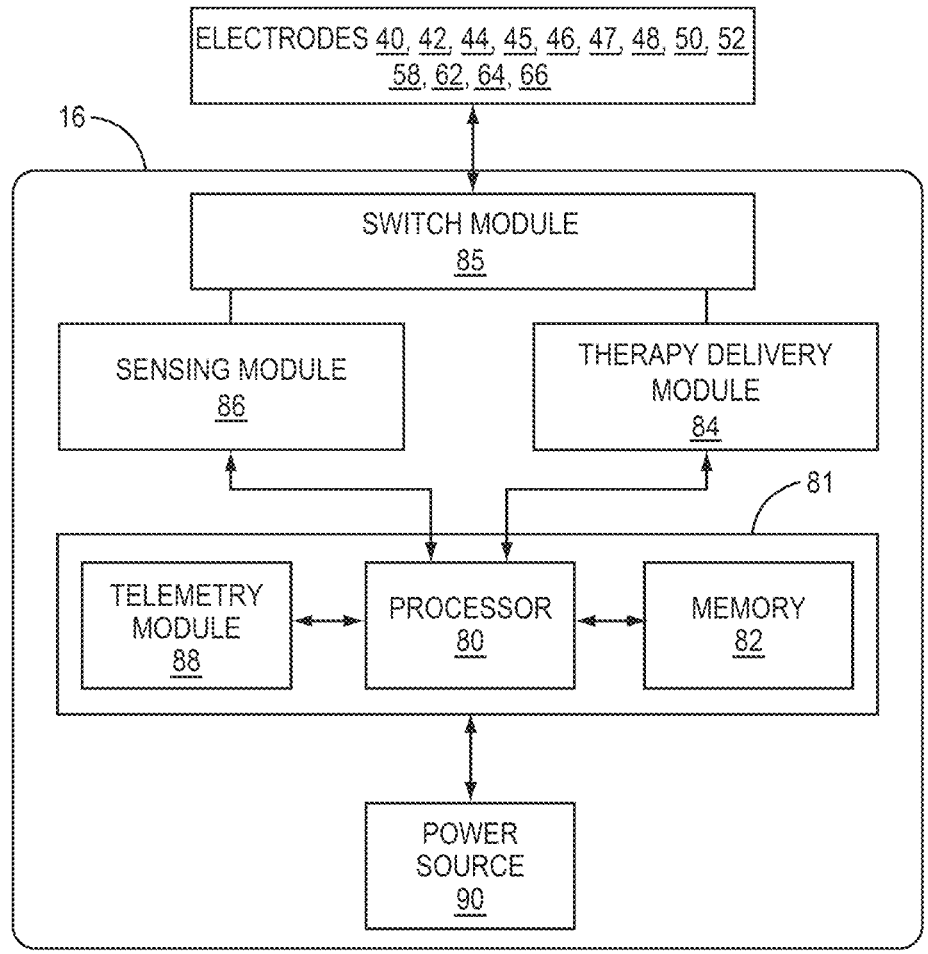
FIG. 9A is a block diagram of an illustrative IMD, e.g., of the systems of FIGS. 1 and 2.

Further, FIG. 9A is a functional block diagram of one illustrative configuration of the IMD 16. As shown, the IMD 16 may include a control module 81 (e.g., a controller), a therapy delivery module 84 (e.g., which may include a stimulation generator), a sensing module 86, and a power source 90. The control module 81 may be operably coupled to the pacing lead 20 and may be configured to deliver pacing therapy to the implant region proximate the at least one septal perforating vein of the patient's heart using at least one electrode of the plurality of electrodes of the pacing lead 20.

The control module, or apparatus, 81 may include a processor 80, memory 82, and a telemetry module, or apparatus, 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random-access memory (RAM), read-only memory (ROM), non-volatile RAM (NVRAM), electrically-erasable programmable ROM (EEPROM), flash memory, and/or any other digital media. An illustrative capture management module may be the left ventricular capture management (LVCM) module described in U.S. Pat. No. 7,684,863 entitled "LV THRESHOLD MEASUREMENT AND CAPTURE MANAGEMENT" and issued Mar. 23, 2010, which is incorporated herein by reference in its entirety.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., A-V delays, V-V delays, pacing pulses with the amplitudes, pulse widths, frequency, or electrode polarities, etc., which may be specified by one or more selected therapy programs (e.g., A-V and/or V-V delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66. In particular, for example, the therapy delivery module 84 may be configured to generate and deliver electrical stimulation therapy such as cardiac conduction system pacing therapy to the cardiac conduction system of the heart 12 using one or more of the electrodes 44, 45, 46, 47. In some embodiments, the therapy delivery module 84 may be configured to generate and deliver electrical stimulation therapy such as traditional cardiac pacing therapy to the heart 12 using one or more of the electrodes 44, 45, 46, 47.

Further, for example, therapy delivery module 84 may deliver pacing stimulus (e.g., pacing pulses) via ring electrodes 40, 44, 45, 46, 47, 48 coupled to leads 18, 20, 22 and/or helical tip electrodes 42, 50 of leads 18, 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a bipolar or multipolar pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt-driven device and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 9B:
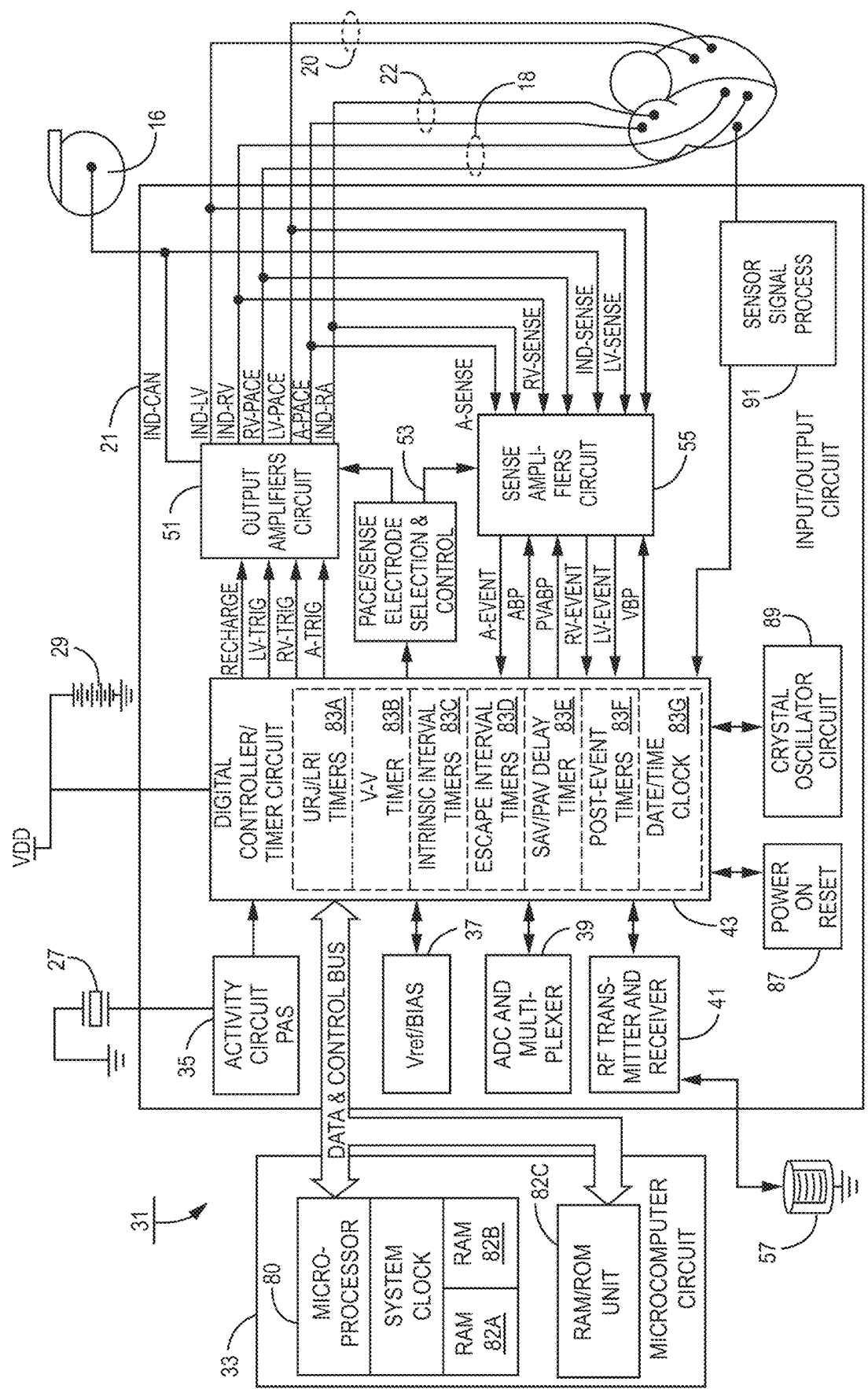
FIG. 9B is another block diagram of an illustrative IMD (e.g., an implantable pulse generator) circuitry and associated leads employed in the systems of FIGS. 1 and 2.

FIG. 9B is another embodiment of a functional block diagram for IMD 16 that depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timing circuit 43 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 43, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21 while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21. Analog-to-digital converter (ADC) and multiplexer circuit 39 digitize analog signals and voltage to provide, e.g., real time telemetry of cardiac signals from sense amplifiers 55 for uplink transmission via RF transmitter and receiver circuit 41. Voltage reference and bias circuit 37, ADC and multiplexer 39, power-on-reset circuit 87, and crystal oscillator circuit 89 may correspond to any of those used in illustrative implantable cardiac pacemakers.

If the IPG is programmed to a rate responsive mode, the signals output by one or more physiologic sensors are employed as a rate control parameter (RCP) to derive a physiologic escape interval. For example, the escape interval is adjusted proportionally to the patient's activity level developed in the patient activity sensor (PAS) circuit 35 in the depicted, illustrative IPG circuit 31. The patient activity sensor 27 is coupled to the IPG housing and may take the form of a piezoelectric crystal transducer. The output signal of the patient activity sensor 27 may be processed and used as an RCP. Sensor 27 generates electrical signals in response to sensed physical activity that are processed by activity circuit 35 and provided to digital controller/timer circuit 43. Activity circuit 35 and associated sensor 27 may correspond to the circuitry disclosed in U.S. Pat. No. 5,052,388 entitled "METHOD AND APPARATUS FOR IMPLEMENTING ACTIVITY SENSING IN A PULSE GENERATOR" and issued on Oct. 1, 1991, and U.S. Pat. No. 4,428,378 entitled "RATE ADAPTIVE PACER" and issued on Jan. 31, 1984, each of which is incorporated herein by reference in its entirety. Similarly, the illustrative systems, apparatus, and methods described herein may be practiced in conjunction with alternate types of sensors such as oxygenation sensors, pressure sensors, pH sensors, and respiration sensors, for use in providing rate responsive pacing capabilities. Alternately, QT time may be used as a rate indicating parameter, in which case no extra sensor is required. Similarly, the illustrative embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities may include the ability to transmit stored digital information, e.g., operating modes and parameters, EGM histograms, and other events, as well as real time EGMs of atrial and/or ventricular electrical activity and marker channel pulses indicating the occurrence of sensed and paced depolarizations in the atrium and ventricle.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 43 and A-EVENT, RV-EVENT, and LV-EVENT signals generated by sense amplifiers circuit 55, among others. The specific values of the intervals and delays timed out by digital controller/timer circuit 43 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative A-V delay intervals, V-V delay intervals, and the energy delivered to each ventricle and/or atrium.

In one embodiment, microprocessor 80 is a custom microprocessor adapted to fetch and execute instructions stored in RAM/ROM unit 82 in a conventional manner. It is contemplated, however, that other implementations may be suitable to practice the present disclosure. For example, an off-the-shelf, commercially available microprocessor or microcontroller, or custom application-specific, hardwired logic, or state-machine type circuit may perform the functions of microprocessor 80.

Digital controller/timer circuit 43 operates under the general control of the microcomputer 33 to control timing and other functions within the pacing circuit 21 and includes a set of timing and associated logic circuits of which certain ones pertinent to the present disclosure are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an A-V delay interval timer 83E for timing the A-LVp delay (or A-RVp delay) from a preceding A-EVENT or A-TRIG, a post-ventricular timer 83F for timing post-ventricular time periods, and a date/time clock 83G.

The A-V delay interval timer 83E is loaded with an appropriate delay interval for one ventricular chamber (e.g., either an A-RVp delay or an A-LVp) to time-out starting from a preceding A-PACE or A-EVENT. The interval timer 83E triggers pacing stimulus delivery and can be based on one or more prior cardiac cycles (or from a data set empirically derived for a given patient).

The post-event timer 83F times out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any A-V delay, and an atrial blanking period (ABP) during which atrial sensing is disabled. It should be noted that the starting of the post-atrial time periods and the A-V delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG.

The microprocessor 80 also optionally calculates A-V delays, V-V delays, post-ventricular time periods, and post-atrial time periods that vary with the sensor-based escape interval established in response to the RCP(s) and/or with the intrinsic atrial and/or ventricular rate.

The output amplifiers circuit 51 contains a RA pace pulse generator (and a LA pace pulse generator if LA pacing is provided), a RV pace pulse generator, a LV pace pulse generator, and/or any other pulse generator configured to provide atrial and ventricular pacing. In order to trigger generation of an RV-PACE or LV-PACE pulse, digital controller/timer circuit 43 generates the RV-TRIG signal at the time-out of the A-RVp delay (in the case of RV pre-excitation) or the LV-TRIG at the time-out of the A-LVp delay (in the case of LV pre-excitation) provided by A-V delay interval timer 83E (or the V-V delay timer 83B). Similarly, digital controller/timer circuit 43 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND-CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 43 controls sensitivity settings of the atrial and ventricular sense amplifiers 55.

The sense amplifiers may be uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV, and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 43. Similarly, left atrial depolarizations or P-waves in the LA-SENSE signal that are sensed by the LA sense amplifier, if provided, result in a LA-EVENT signal that is communicated to the digital controller/timer circuit 43. Ventricular depolarizations or R-waves in the RV-SENSE signal are sensed by a ventricular sense amplifier result in an RV-EVENT signal that is communicated to the digital controller/timer circuit 43. Similarly, ventricular depolarizations or R-waves in the LV-SENSE signal are sensed by a ventricular sense amplifier result in an LV-EVENT signal that is communicated to the digital controller/timer circuit 43. The RV-EVENT, LV-EVENT, and RA-EVENT, LA-SENSE signals may be refractory or non-refractory and can inadvertently be triggered by electrical noise signals or aberrantly conducted depolarization waves rather than true R-waves or P-waves.

The techniques described in this disclosure, including those attributed to the IMD 16 and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by processing circuitry and/or one or more processors to support one or more aspects of the functionality described in this disclosure.

ILLUSTRATIVE EMBODIMENTS

While the present disclosure is not so limited, an appreciation of various aspects of the disclosure will be gained through a discussion of the specific examples and illustrative embodiments provided below. Various modifications of the examples and illustrative embodiments, as well as additional embodiments of the disclosure, will become apparent herein.

A1. A method of implanting pacing lead in a patient's heart, the method comprising:
  inserting a catheter through coronary sinus ostium of the patient's heart;

moving the catheter to position a distal end region of the catheter into the great cardiac vein past the anterolateral vein of the patient to one or more positions proximate at least one septal perforating vein of the patient;

injecting contrast out of the distal end region of the catheter into an injection area of each of the one or more positions proximate the at least one septal perforating vein;

identifying an implant region proximate the at least one septal perforating vein;

removing the catheter; and moving a pacing lead to the implant region to deliver pacing therapy thereto.

A2. The method of embodiment A1, wherein the one or more positions comprises a plurality of positions.

A3. The method of any preceding A embodiment, further comprising positioning, using the catheter, a guide wire proximate the identified implant region, wherein moving a pacing lead to the implant region comprises moving the pacing lead to the implant region using the guide wire.

A4. The method of any preceding A embodiment, wherein the catheter comprises a distal balloon and a proximal balloon positioned on the distal end region, the distal balloon located more distally than the proximal balloon, the method further comprising inflating the distal and proximal balloons to block blood flow to the injection area between the distal and proximal balloons prior to injecting contrast into the injection area.

A5. The method of any preceding A embodiment, wherein the catheter defines one or more side openings in the distal end region, wherein injecting contrast comprises ejecting contrast from the one or more side openings.

A6. The method of any preceding A embodiment, further comprising creating great cardiac vein map using contrast injected at the one or more positions.

A7. The method of any preceding A embodiment, further comprising advancing an actively steerable catheter into the great cardiac vein after removing the catheter to navigate the at least one septal perforating vein.

A8. The method of any preceding A embodiment, further comprising navigating the at least one septal perforating vein using the catheter, wherein the distal end region of the catheter defines a spiral tip.

A9. The method of any preceding A embodiment, wherein the implant region provides cardiac conduction system pacing, wherein the pacing lead delivers cardiac conduction system pacing to the implant region.

A10. The method of any preceding A embodiment, wherein the implant region is proximate the His bundle, wherein the pacing lead delivers His bundle pacing to the implant region.

A11. The method of any preceding A embodiment, wherein the implant region is proximate the left bundle branch pacing, wherein the pacing lead delivers left bundle branch pacing to the implant region.

A12. The method of any preceding A embodiment, further comprising imaging the patient's heart by CT/MR angiography scope prior to inserting the catheter.

A13. The method of any preceding A embodiment, further comprising imaging the patient's heart by rotational angiography prior to inserting the catheter.

A14. The method of any preceding A embodiment, further comprising positioning an imaging crosshead according to the preferred view prior to inserting the catheter.

A15. The method of any preceding A embodiment, further comprising generating a cardiac map of electrical activation based on a plurality of electrode signals monitored using a plurality of external electrodes proximate the skin on the patient.

B1. A method of identifying an implant region in a patient's heart, the method comprising:

inserting a catheter through the coronary sinus ostium of the patient's heart;

moving the catheter to position a distal end region of the catheter into the great cardiac vein past the anterolateral vein of the patient to one or more positions proximate at least one septal perforating vein of the patient, wherein the catheter comprises a distal balloon and a proximal balloon positioned on the distal end region, the distal balloon located more distally than the proximal balloon;

inflating the distal and proximal balloons to block blood flow to an injection area between the distal and proximal balloons at each of the one more positions;

injecting contrast out of the distal end region of the catheter into an injection area of each of the one or more positions proximate the at least one septal perforating vein; and identifying an implant region proximate the at least one septal perforating vein.

B2. The method of embodiment B1, further comprising:

deflating the distal and proximal balloons after injecting contrast;

moving the catheter to another position of the one or more positions;

inflating the distal and proximal balloons to block blood flow to another injection area between the distal and proximal balloons; and injecting contrast into the injection area of the another position of the one or more positions proximate the at least one septal perforating vein.

B3. The method of any preceding B embodiment, further comprising:

removing the catheter; and moving a pacing lead to the implant region to delivery pacing therapy thereto.

B4. The method of embodiment B3, further comprising positioning, using the catheter, a guide wire proximate the identified implant region, wherein moving a pacing lead to the implant region comprises moving the pacing lead to the implant region using the guide wire.

B5. The method of any preceding B embodiment, wherein the catheter defines one or more side openings in the distal end region, wherein injecting contrast comprises ejecting contrast from the one or more side openings.

B6. The method of any preceding B embodiment, further comprising creating great cardiac vein map using contrast injected at the one or more positions.

B7. The method of any preceding B embodiment, further comprising advancing an actively steerable catheter into the great cardiac vein after removing the catheter to navigate the at least one septal perforating vein.

B8. The method of any preceding B embodiment, further comprising navigating the at least one septal perforating vein using the catheter, wherein the distal end region of the catheter defines a spiral tip.

B9. The method of any preceding B embodiment, further comprising imaging the patient's heart by CT/MR angiography scope prior to inserting the catheter.

B10. The method of any preceding B embodiment, further comprising positioning an imaging crosshead according to the preferred view prior to inserting the catheter.

B11. The method of any preceding B embodiment, further comprising imaging the patient's heart by rotational angiography prior to inserting the catheter.

C1. A catheter comprising:
- an elongate housing extending between a proximal end region and a distal end region and positionable in the great cardiac vein such that the distal end region is located past the anterolateral vein of the patient proximate at least one septal perforating vein of the patient, wherein the elongate housing defines a lumen extending therethrough, wherein the elongate housing further defines one or more side openings extending through an outer surface of the elongate housing in the distal end region of the elongate housing and in fluid communication with the lumen, wherein contrast is configured to be injected through the one or more side openings of the elongate housing into an injection area proximate the at least one septal perforating vein; and
- at least two inflatable balloons positioned on the distal end region of the elongate housing, wherein the at least two inflatable balloons comprise a first inflatable balloon positioned distally of the one or more side openings and a second inflatable balloon positioned proximally of the one or more side openings.

C2. The catheter of embodiment C1, wherein the elongate housing further defines a guide wire lumen and the catheter further comprises a guide wire configured to extend through the guide wire lumen.

C3. The catheter of embodiment C2, wherein the elongate housing further defines a guide wire opening extending through the outer surface of the elongate housing and in fluid communication with the guide wire lumen such that the guide wire exits the guide wire lumen through the guidewire opening, wherein the guide wire opening is positioned between the first and second inflatable balloons.

C4. The catheter of any preceding C embodiment, wherein the at least two inflatable balloons inflate to block blood flow to the injection area between the first and second balloons prior to injecting contrast into the injection area.

C5. The catheter of any preceding C embodiment, further comprising one or more radiopaque marker bands.

C6. The catheter of embodiment C5, wherein the one or more radiopaque marker bands are located on the elongate housing proximate the first and second inflatable balloons.

C7. The catheter of embodiment C5, wherein the one or more radiopaque marker bands define directional markers.

C8. The catheter of any preceding C embodiment, wherein the at least two inflatable balloons comprise a compliant material.

C9. The catheter of any preceding C embodiment, wherein the first balloon defines a first diameter when inflated and the second balloon defines a second diameter when inflated, wherein the first diameter is smaller than the second diameter.

C10. The catheter of any preceding C embodiment, wherein the first and second balloons are spaced apart by 0.5 inches to 1 inch.

C11. The catheter of any preceding C embodiment, wherein the elongate housing further defines a bypass lumen.

C12. The catheter of any preceding C embodiment, wherein the at least two inflatable balloons further comprise a third balloon and a fourth balloon, wherein the one or more side openings comprises a first opening located between the first and second balloons and a second opening located between the third and fourth balloons.

C13. The catheter of any preceding C embodiment, wherein the distal end region of the catheter defines a spiral tip configured to navigate the at least one septal perforating vein.

D1. A pacing device comprising:
- a pacing lead extending between a proximal end region and a distal end region, wherein the pacing lead comprises a plurality of electrodes proximate the distal end region, wherein the distal end region of the pacing lead is positionable in an implant region proximate at least one septal perforating vein of a patient's heart; and
- a controller comprising one or more processors and operably coupled to the pacing lead, wherein the controller is configured to deliver pacing therapy to the implant region proximate the at least one septal perforating vein of the patient's heart using at least one electrode of the plurality of electrodes of the pacing lead.

D2. The pacing device of embodiment D1, wherein the distal end region of the pacing lead defines a diameter of less than or equal to 1 millimeter.

D3. The pacing device of any preceding D embodiment, wherein the implant region is proximate the cardiac conduction system of the patient's heart, wherein the pacing therapy comprises cardiac conduction system pacing therapy.

D4. The pacing device of any preceding D embodiment, wherein the implant region is proximate the His bundle of the patient's heart, wherein the pacing therapy comprises His bundle pacing therapy.

D5. The pacing device of any preceding D embodiment, wherein the implant region is proximate the left bundle branch pacing of the patient's heart, wherein the pacing therapy comprises left bundle branch pacing therapy.

D6. The pacing device of any preceding D embodiment, wherein the pacing lead comprises a quadripolar lead.

D7. The pacing device of any preceding D embodiment, wherein the pacing lead comprises a unipolar lead E1. A system for delivering pacing therapy to a patient's heart, the system comprising:
- a catheter comprising an elongate housing extending between a proximal end region and a distal end region, wherein the elongate housing defines a lumen extending therethrough, wherein the catheter is configured to be inserted through the coronary sinus ostium of a patient's heart such that the distal end region of the catheter is positioned into the great cardiac vein past the anterolateral vein of the patient proximate at least one septal perforating vein of the patient's heart, wherein the catheter is further configured to inject contrast into an injection area proximate the at least one septal perforating vein;
- a pacing lead extending between a proximal end region and a distal end region, wherein the pacing lead comprises a plurality of electrodes proximate the distal end region, wherein the distal end region of the pacing lead is positionable in an implant region proximate the at least one septal perforating vein and the injection area; and
- a controller operably coupled to the pacing lead and configured to deliver pacing therapy to the implant region, through at least one electrode of the plurality of electrodes, when the distal end region of the pacing lead is positioned in the implant region.

E2. The system of embodiment E1, wherein the catheter further comprises at least two inflatable balloons on the distal end region and inflatable to block blood flow to the injection area prior to injecting contrast into the injection area.

E3. The system of embodiment E2, wherein the at least two inflatable balloons comprise a first inflatable balloon and a second inflatable balloon, wherein the first and second balloons are spaced apart by 0.5 inches to 1 inch.

E4. The system of any preceding E embodiment, further comprising an actively steerable catheter configured to be advanced through the great cardiac vein after removing the catheter and to navigate the at least one septal perforating vein.

E5. The system of any preceding E embodiment, wherein the elongate housing further defines one or more side openings extending through an outer surface of the elongate housing in the distal end region of the elongate housing and in fluid communication with the lumen, wherein the catheter is configured to inject contrast through the one or more side openings.

E6. The system of any preceding E embodiment, wherein the distal end region of the catheter defines a spiral tip configured to navigate the at least one septal perforating vein.

E7. The system of any preceding E embodiment, wherein the elongate housing further defines a guide wire lumen and the system further comprises a guide wire configured to extend through the guide wire lumen.

E8. The system of any preceding E embodiment, wherein the catheter comprises one or more radiopaque marker bands.

E9. The system of any preceding E embodiment, wherein the distal end region of the pacing lead defines a diameter of less than or equal to 1 millimeter.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. A method of implanting pacing lead in a patient's heart, the method comprising:
    inserting a catheter through coronary sinus ostium of the patient's heart;
    moving the catheter to position a distal end region of the catheter into the great cardiac vein past the anterolateral vein of the patient to one or more positions proximate at least one septal perforating vein of the patient;
    injecting contrast out of the distal end region of the catheter into an injection area of each of the one or more positions proximate the at least one septal perforating vein;
    identifying an implant region proximate the at least one septal perforating vein;
    removing the catheter; and
    moving a pacing lead to the implant region to deliver pacing therapy thereto.

2. The method of claim 1, wherein the one or more positions comprises a plurality of positions.

3. The method of claim 1, further comprising positioning, using the catheter, a guide wire proximate the identified implant region, wherein moving a pacing lead to the implant region comprises moving the pacing lead to the implant region using the guide wire.

4. The method of claim 1, wherein the catheter comprises a distal balloon and a proximal balloon positioned on the distal end region, the distal balloon located more distally than the proximal balloon, the method further comprising inflating the distal and proximal balloons to block blood flow to the injection area between the distal and proximal balloons prior to injecting contrast into the injection area.

5. The method of claim 1, wherein the catheter defines one or more side openings in the distal end region, wherein injecting contrast comprises ejecting contrast from the one or more side openings.

6. The method of claim 1, further comprising creating great cardiac vein map using contrast injected at the one or more positions.

7. The method of claim 1, further comprising advancing an actively steerable catheter into the great cardiac vein after removing the catheter to navigate the at least one septal perforating vein.

8. The method of claim 1, wherein the implant region provides cardiac conduction system pacing, wherein the pacing lead delivers cardiac conduction system pacing to the implant region.

9. The method of claim 8, where the cardiac conduction system pacing comprises one or both of left bundle branch pacing and right bundle branch pacing.

10. The method of claim 1, further comprising imaging the patient's heart by CT/MR angiography scope prior to inserting the catheter.

11. A pacing device comprising:
    a pacing lead extending between a proximal end region and a distal end region, wherein the pacing lead comprises a plurality of electrodes proximate the distal end region, wherein the distal end region of the pacing lead is positionable in an implant region proximate at least one septal perforating vein of a patient's heart; and
    a controller comprising one or more processors and operably coupled to the pacing lead, wherein the controller is configured to deliver pacing therapy to the implant region proximate the at least one septal perforating vein of the patient's heart using at least one electrode of the plurality of electrodes of the pacing lead.

12. The pacing device of claim 11, wherein the implant region is proximate the cardiac conduction system of the patient's heart, wherein the pacing therapy comprises cardiac conduction system pacing therapy.

13. The pacing device of claim 11, wherein the pacing lead comprises a quadripolar lead.

14. The pacing device of claim 11, wherein the pacing lead comprises a unipolar lead.

15. A system for delivering pacing therapy to a patient's heart, the system comprising:
    a catheter comprising an elongate housing extending between a proximal end region and a distal end region, wherein the elongate housing defines a lumen extending therethrough, wherein the catheter is configured to be inserted through the coronary sinus ostium of a patient's heart such that the distal end region of the catheter is positioned into the great cardiac vein past the anterolateral vein of the patient proximate at least one septal perforating vein of the patient's heart, wherein the catheter is further configured to inject contrast into an injection area proximate the at least one septal perforating vein;
    a pacing lead extending between a proximal end region and a distal end region, wherein the pacing lead comprises a plurality of electrodes proximate the distal end region, wherein the distal end region of the pacing lead is positionable in an implant region proximate the at least one septal perforating vein and the injection area; and a controller operably coupled to the pacing lead and configured to deliver pacing therapy to the implant region, through at least one electrode of the plurality of electrodes, when the distal end region of the pacing lead is positioned in the implant region.

16. The system of claim 15, wherein the catheter further comprises at least two inflatable balloons on the distal end region and inflatable to block blood flow to the injection area prior to injecting contrast into the injection area.

17. The system of claim 15, wherein the elongate housing further defines one or more side openings extending through an outer surface of the elongate housing in the distal end region of the elongate housing and in fluid communication with the lumen, wherein the catheter is configured to inject contrast through the one or more side openings.

18. The system of claim 15, wherein the catheter comprises one or more radiopaque marker bands.

19. The system of claim 15, wherein the distal end region of the pacing lead defines a diameter of less than or equal to 1 millimeter.

20. The system of claim 15, wherein the implant region is proximate one or both of the left bundle branch and the right bundle branch of the cardiac conduction system, wherein the pacing therapy comprises cardiac conduction system pacing therapy to one or both of the left bundle branch and the right bundle branch.

* * * * *